(12) United States Patent
Day et al.

(10) Patent No.: US 10,184,952 B2
(45) Date of Patent: *Jan. 22, 2019

(54) SYSTEM AND METHOD FOR SPEED SENSOR POSITION DETECTION IN A MULTIPLE CHANNEL CONTROL SYSTEM

(71) Applicant: PRATT & WHITNEY CANADA CORP., Longueuil (CA)

(72) Inventors: Christopher Day, Mississauga (CA); Royston D'Souza, Mississauga (CA); Faran Hafeez, Mississauga (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 177 days.

This patent is subject to a terminal disclaimer.

(21) Appl. No.: 15/172,796

(22) Filed: Jun. 3, 2016

(65) Prior Publication Data

US 2016/0327589 A1 Nov. 10, 2016

Related U.S. Application Data

(63) Continuation of application No. 14/155,735, filed on Jan. 15, 2014, now Pat. No. 9,383,385.

(51) Int. Cl.
*G01P 21/00* (2006.01)
*G01M 15/14* (2006.01)
*G01N 29/04* (2006.01)
*G01N 29/14* (2006.01)
*G01P 3/488* (2006.01)
*G01P 3/489* (2006.01)

(52) U.S. Cl.
CPC ............ *G01P 21/00* (2013.01); *G01M 15/14* (2013.01); *G01N 29/04* (2013.01); *G01N 29/14* (2013.01); *G01P 3/488* (2013.01); *G01P 3/489* (2013.01); *G01N 2291/2693* (2013.01)

(58) Field of Classification Search
CPC ....................................................... G01P 21/00
See application file for complete search history.

(56) References Cited

U.S. PATENT DOCUMENTS

| | | | |
|---|---|---|---|
| 5,365,904 | A | 11/1994 | Nofsinger et al. |
| 6,741,919 | B1 | 5/2004 | Schuster et al. |
| 7,769,510 | B2 | 8/2010 | Dehholm et al. |
| RE42,464 | E | 6/2011 | Nada |
| 2015/0096371 | A1 | 4/2015 | O'Neil et al. |

*Primary Examiner* — Robert R Raevis
(74) *Attorney, Agent, or Firm* — Norton Rose Fulbright Canada LLP

(57) ABSTRACT

A system and method for detection of speed sensor position in an engine comprising speed sensors and a controller having channels each operatively connected to a different one of the speed sensors. A memory stores predetermined sensor position arrangements each identifying, for each one of the channels, a speed sensor connected to the channel, and predetermined engine parameter values each associated with a corresponding predetermined sensor position arrangement. A current engine parameter value is computed on the basis of received input data. The predetermined sensor position arrangements and the predetermined engine parameter values are retrieved from the memory and a predetermined engine parameter value that matches the current engine parameter value is determined. The predetermined sensor position arrangement associated with the predetermined engine parameter value is then identified and, for each one of the channels, the speed sensor currently connected to the channel is determined.

20 Claims, 11 Drawing Sheets

| Case | Channel A | Channel B | Delta angle (degrees) |
|---|---|---|---|
| 1 | Sensor # 1 | Sensor # 3 | 111.0 |
| 2 | Sensor # 1 | Sensor # 2 | 241.0 |
| 3 | Sensor # 2 | Sensor # 1 | 119.0 |
| 4 | Sensor # 2 | Sensor # 3 | 230.0 |
| 5 | Sensor # 3 | Sensor # 2 | 130.0 |
| 6 | Sensor # 3 | Sensor # 1 | 249.0 |

Fig. 7

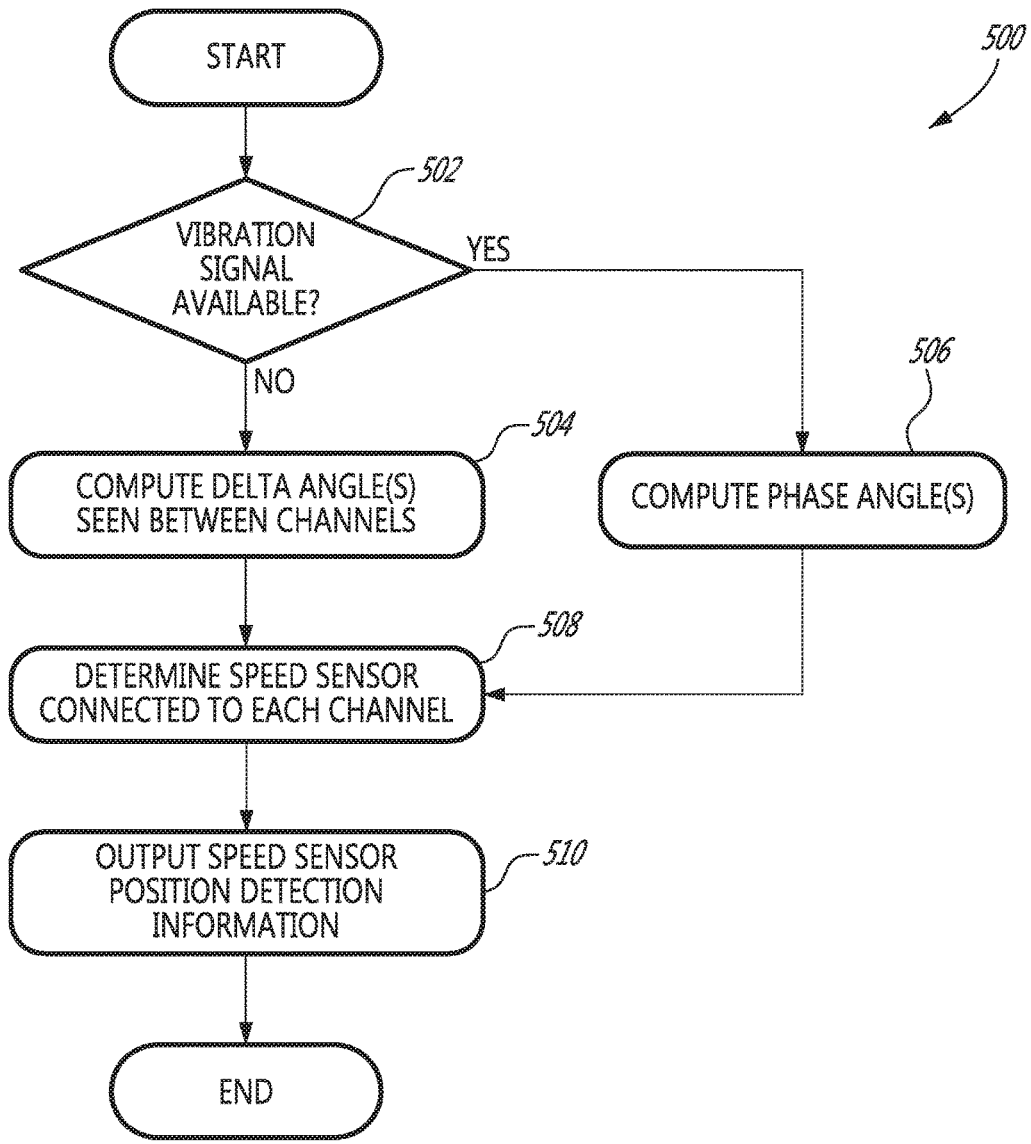

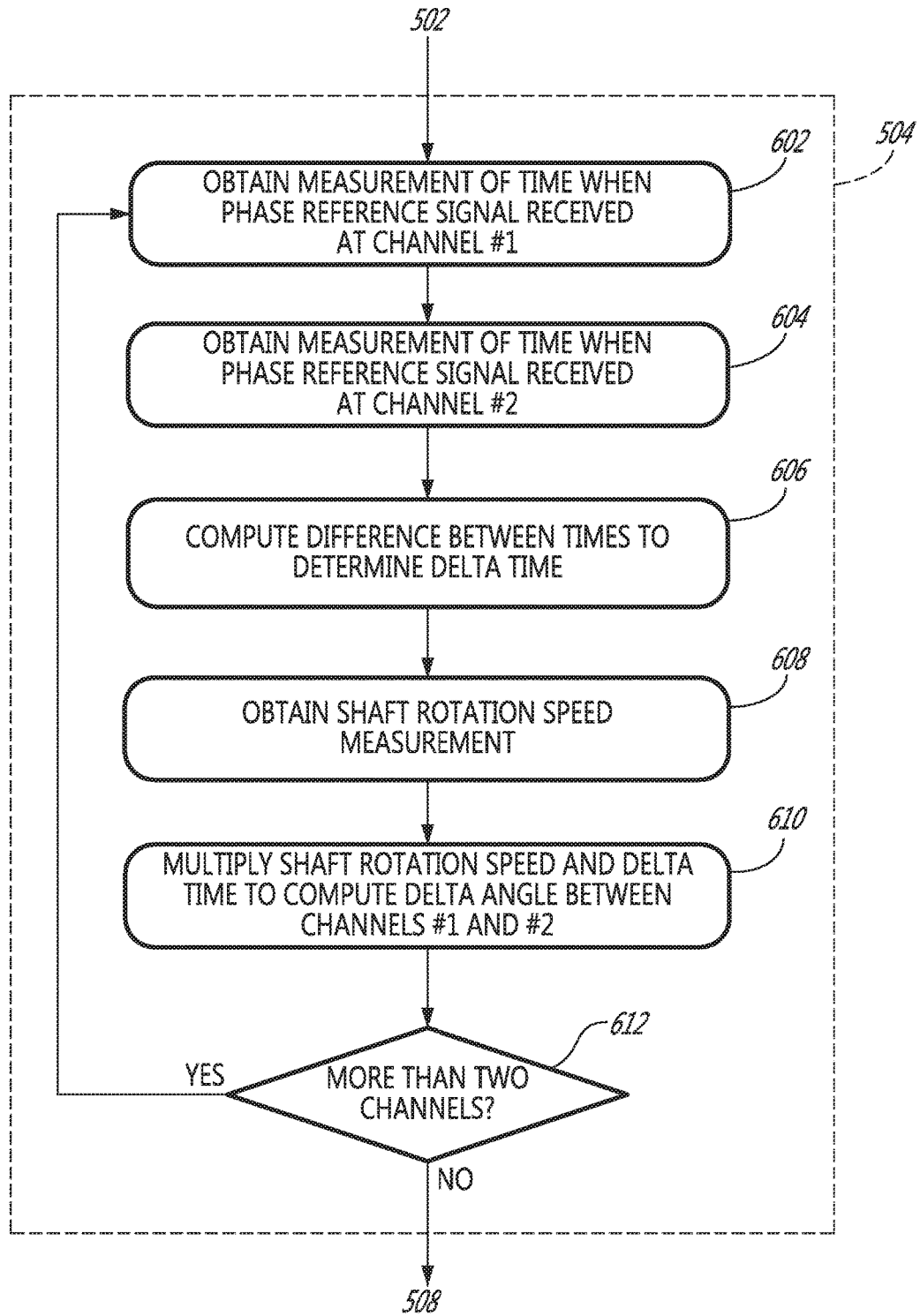

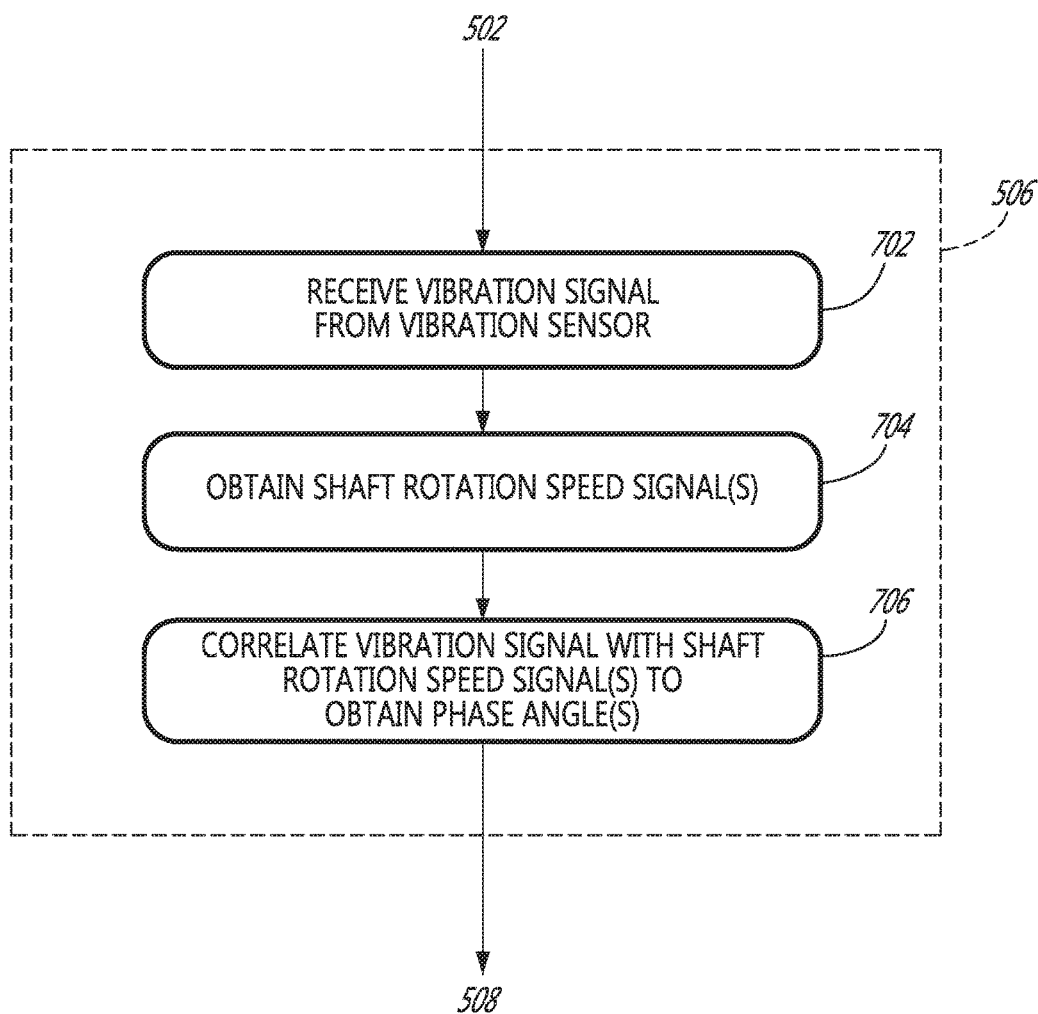

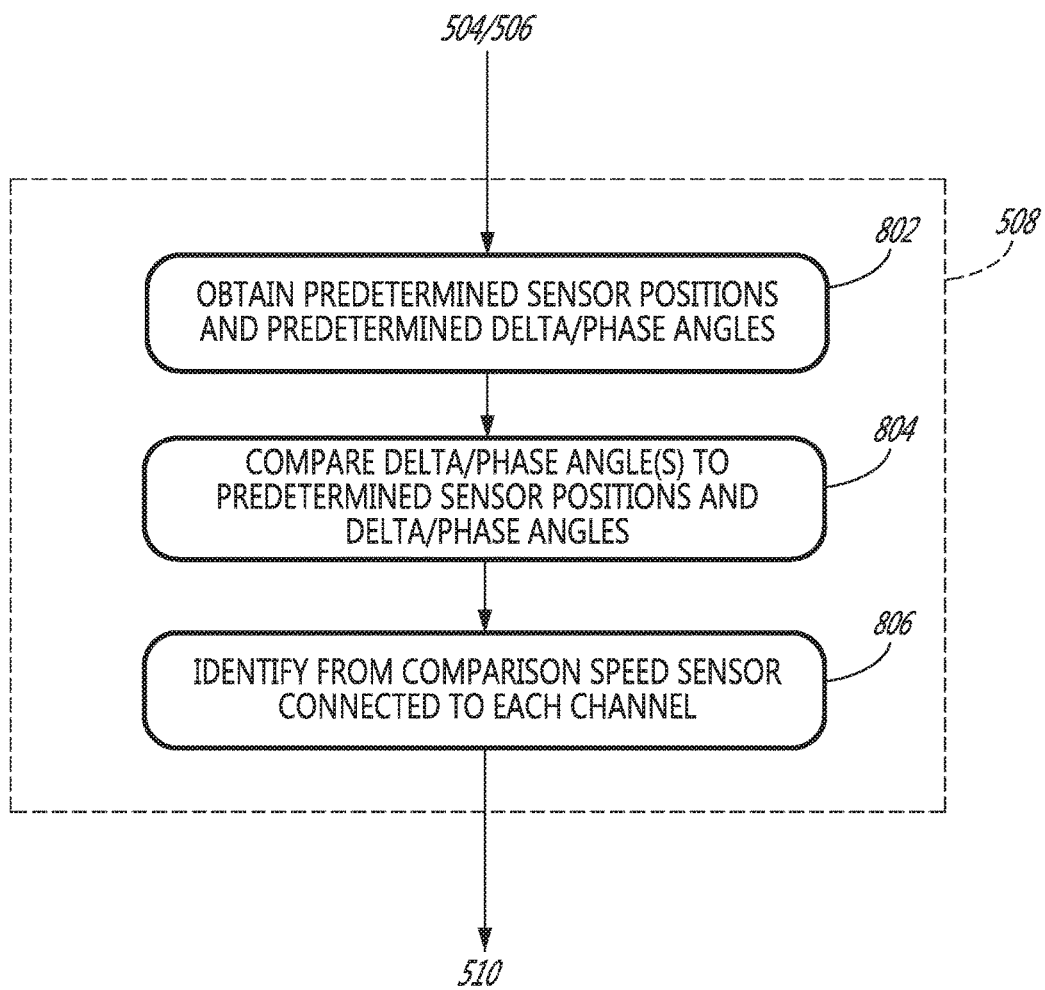

SYSTEM AND METHOD FOR SPEED SENSOR POSITION DETECTION IN A MULTIPLE CHANNEL CONTROL SYSTEM

CROSS-REFERENCE TO RELATED APPLICATIONS

This application is a continuation of U.S. patent application Ser. No. 14/155,735, the contents of which are hereby incorporated by reference.

TECHNICAL FIELD

The application relates generally to the control of gas turbine engines.

BACKGROUND OF THE ART

Aircraft engines typically require manual or automated assembly operations to ensure proper installation and accurate connection of sensors to channels of the engine's controller. Engines are sometimes provided with more sensors of a particular type than control channels exist in the controller, some sensors being connected to the controller while others are left as unconnected spares, the spare sensors remaining disconnected from the controller until, for example, failure of a connected sensor must be remedied. However, where the sensors are not all provided in identical locations or measure data identically, the engine controller must be connected to the correct sensors (and unconnected to the intended spares) in order to correctly interpret received data. Thus, additional care is needed during assembly to ensure that the correct sensors are connected, and the intended spares remain unconnected, to the controller.

There is therefore a need for improved systems and methods for control of gas turbine engines.

SUMMARY

In one aspect, there is provided a system for detection of speed sensor position in an engine, the engine comprising a plurality of speed sensors provided in different circumferential positions about at least one shaft of the engine, each one of the plurality of speed sensors configured for measuring a rotational speed of the at least one shaft, and a multi-channel controller having a plurality of control channels, each one of the plurality of control channels operatively connected to a different one of the plurality of speed sensors for receiving sensor data therefrom. The system comprises a memory having stored therein a plurality of predetermined sensor position arrangements, each identifying, for each one of the plurality of control channels, a selected one of the plurality of speed sensors connected to the control channel, and a plurality of predetermined values of at least one parameter associated with the engine, each of the plurality of predetermined values of the at least one parameter having associated therewith a corresponding one of the plurality of predetermined sensor position arrangements. The system also comprises a processing unit adapted to receive input data comprising the sensor data received from the plurality of speed sensors, compute on the basis of the input data a current value of the at least one parameter, retrieve from the memory the plurality of predetermined sensor position arrangements and the plurality of predetermined values of the at least one parameter, determine a selected one of the plurality of predetermined values of the at least one parameter that matches the current value of the at least one parameter, and identify the corresponding one of the plurality of predetermined sensor position arrangements associated with the selected one of the plurality of predetermined values of the at least one parameter and determine therefrom, for each one of the plurality of control channels, the selected one of the plurality of speed sensors currently connected to the control channel.

In another aspect, there is provided a method for detection of speed sensor position in an engine, the engine comprising a plurality of speed sensors provided in different circumferential positions about at least one shaft of the engine, each one of the plurality of speed sensors configured for measuring a rotational speed of the at least one shaft, and a multi-channel controller having a plurality of control channels, each one of the plurality of control channels operatively connected to a different one of the plurality of speed sensors forproviding sensor data to the multi-channel controller. The method comprises storing a plurality of predetermined sensor position arrangements, each identifying, for each one of the plurality of control channels, a selected one of the plurality of speed sensors connected to the control channel, and a plurality of predetermined values of at least one parameter associated with the engine, each of the plurality of predetermined values of the at least one parameter having associated therewith a corresponding one of the plurality of predetermined sensor position arrangements; receiving input data comprising the sensor data received from the plurality of speed sensors; computing on the basis of the input data a current value of at least one parameter; retrieving the plurality of predetermined sensor position arrangements and the plurality of predetermined values of the at least one parameter; determining a selected one of the plurality of predetermined values of the at least one parameter that matches the current value of the at least one parameter; and identifying the corresponding one of the plurality of predetermined sensor position arrangements associated with the selected one of the plurality of predetermined values of the at least one parameter and determining therefrom, for each one of the plurality of control channels, the selected one of the plurality of speed sensors currently connected to the control channel.

In a further aspect, there is provided a system for detection of speed sensor position in an engine, the engine comprising a plurality of speed sensors provided in different circumferential positions about at least one shaft of the engine, each one of the plurality of speed sensors configured for measuring a rotational speed of the at least one shaft, and a multi-channel controller having a plurality of control channels, each one of the plurality of control channels operatively connected to a different one of the plurality of speed sensors forproviding sensor data to the multi-channel controller. The system comprises means for storing a plurality of predetermined sensor position arrangements, each identifying, for each one of the plurality of control channels, a selected one of the plurality of speed sensors connected to the control channel, and a plurality of predetermined values of at least one parameter associated with the engine, each of the plurality of predetermined values of the at least one parameter having associated therewith a corresponding one of the plurality of predetermined sensor position arrangements; means for receiving input data comprising the sensor data received from the plurality of speed sensors; means for computing on the basis of the input data a current value of at least one parameter; means for retrieving the plurality of predetermined sensor position arrangements and the plurality of predetermined values of the at least one parameter; means for determining a selected one of the plurality of predetermined values of the at least one parameter that matches the current value of the at least one parameter; and means for identifying the corresponding one of the plurality of predetermined sensor position arrangements associated with the selected one of the plurality of predetermined values of the at least one parameter and determining therefrom, for each one of the plurality of control channels, the selected one of the plurality of speed sensors currently connected to the control channel.

DESCRIPTION OF THE DRAWINGS

Reference is now made to the accompanying figures in which:

FIG. 7 is a table illustrating the relationship between sensor position combination and delta angle value for various cases, in accordance with an illustrative embodiment;

FIG. 8 is a flowchart of a method for speed sensor position detection, in accordance with an illustrative embodiment;

FIG. 9 is a flowchart of the step of FIG. 8 of computing a delta angle seen between channels;

FIG. 10 is a flowchart of the step of FIG. 8 of computing a phase angle; and

FIG. 11 is a flowchart of the step of FIG. 8 of determining the speed sensor connected to each channel.

DETAILED DESCRIPTION

Figure 1:
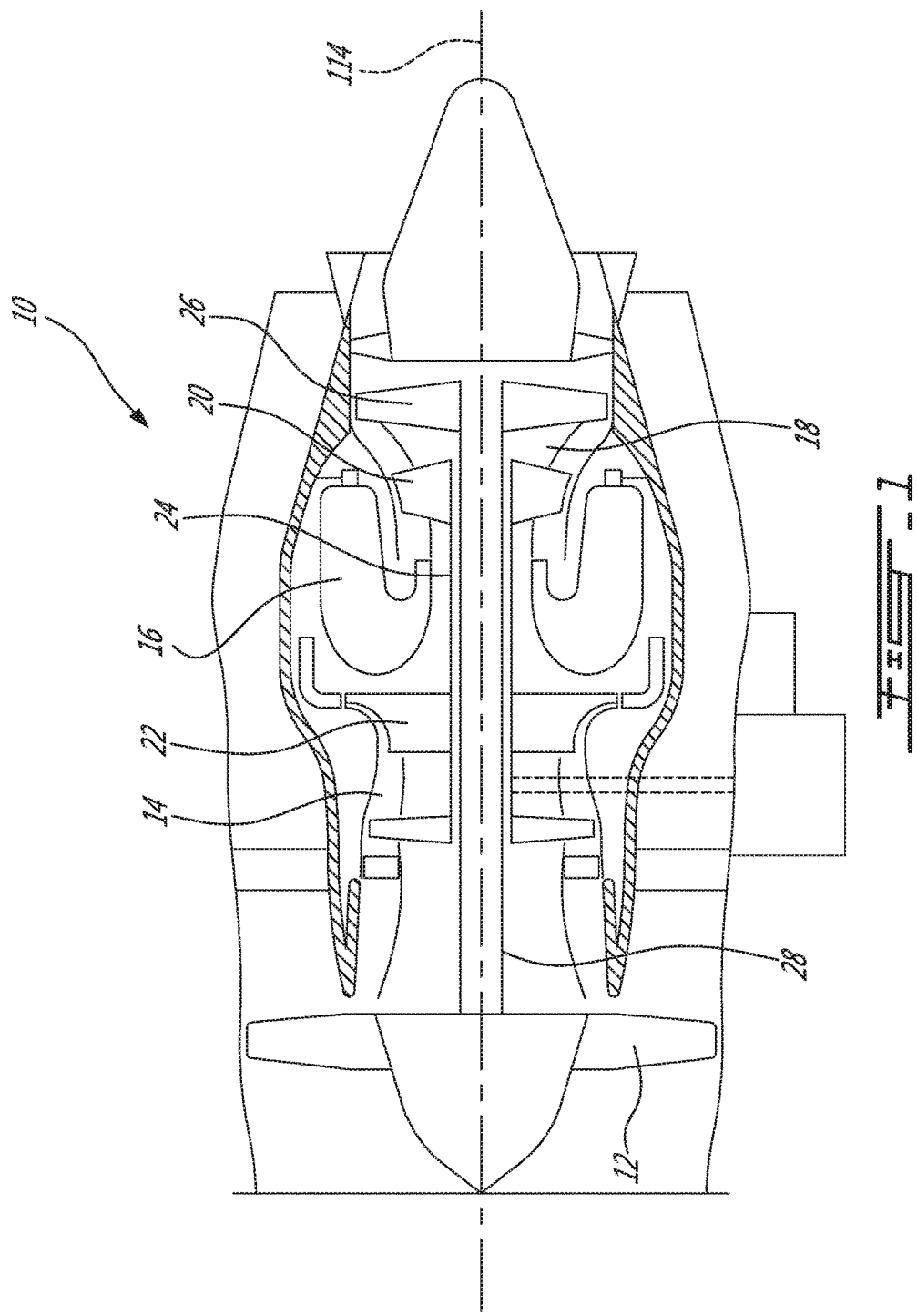
FIG. 1 is a schematic cross-sectional view of a gas turbine engine.

FIG. 1 illustrates a gas turbine engine 10 of a type typically provided for use in subsonic flight, generally comprising in serial flow communication a fan 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases. High pressure rotor(s) 20 of the turbine section 18 are drivingly engaged to high pressure rotor(s) 22 of the compressor section 14 through a high pressure shaft 24. Low pressure rotor(s) 26 of the turbine section 18 are drivingly engaged to the fan rotor 12 and to other low pressure rotor(s) (not shown) of the compressor section 14 through a low pressure shaft 28 extending within the high pressure shaft 24 and rotating independently therefrom.

Although illustrated as a turbofan engine, the gas turbine engine 10 may alternatively be another type of engine, for example a turboshaft engine, also generally comprising in serial flow communication a compressor section, a combustor, and a turbine section, and a fan through which ambient air is propelled. A turboprop engine may also apply.

Figure 2:
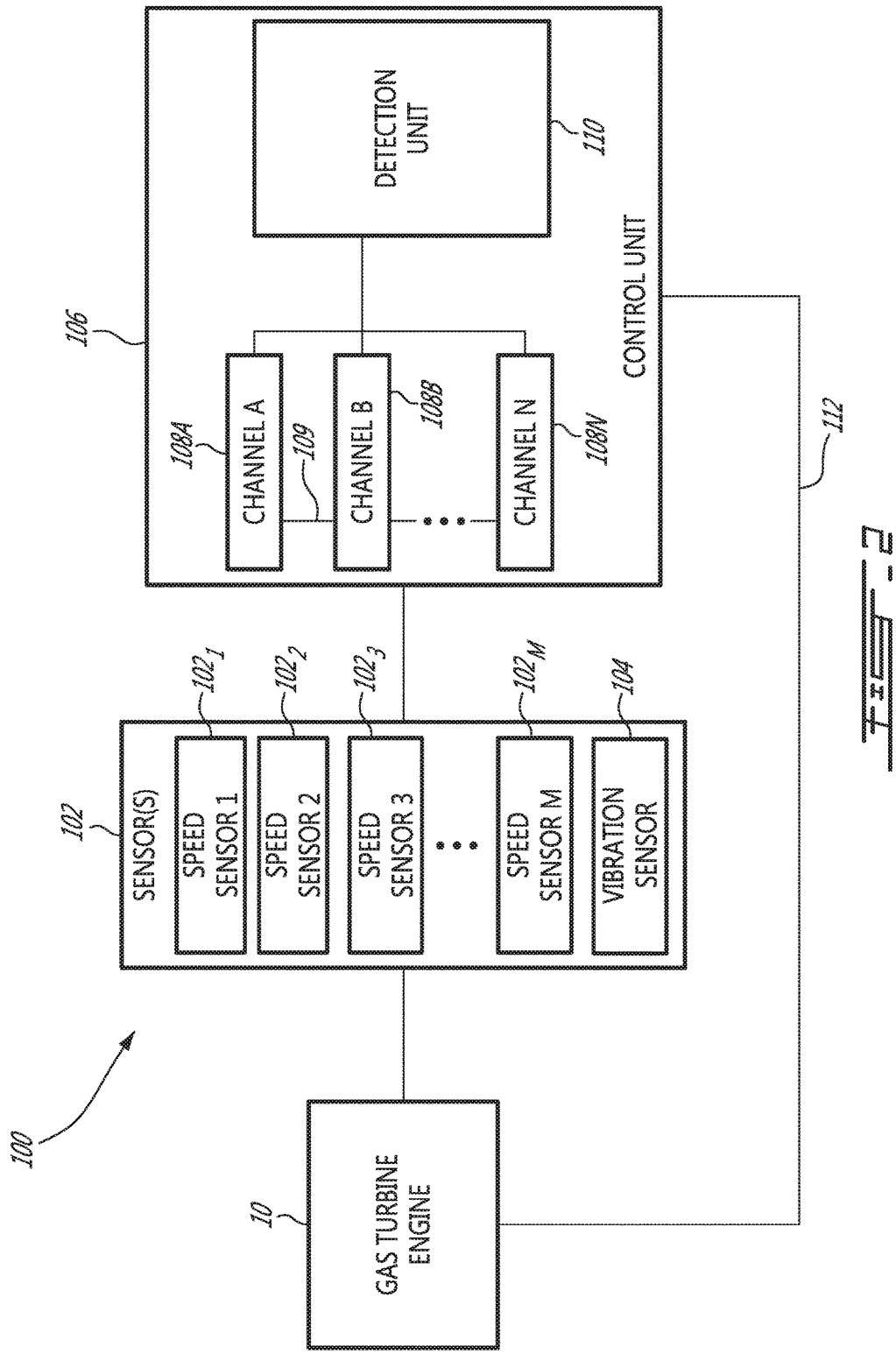
FIG. 2 is a schematic diagram of a speed sensor position detection system, in accordance with an illustrative embodiment.

Referring now to FIG. 2, a system 100 for speed sensor position detection will now be described. The system 100 illustratively comprises a plurality of sensors 102 installed on the engine 10 and comprising a number M of speed sensors as in $102_1, 102_2, \ldots, 102_M$, and a vibration sensor 104 operative to detect vibrations of the engine 10. It should be understood that other sensors may be provided. The sensors 102 are in communication with a control unit 106 and output thereto sensor signals indicative of the sensor measurements.

The control unit 106 illustratively comprises one or more computing devices including, but not limited to, a digital computer, a processor (e.g. a microprocessor), and a memory, in communication with the hardware of the engine 10 for controlling an operation thereof. The control unit 106 is illustratively a multi-channel controller comprising a number N of independent channels as in 108A, 108B, ..., 108N where all control functions are duplicated in the channels 108A, 108B, ..., 108N. Each channel 108A, 108B, ..., 108N illustratively receives the sensor signals from a speed sensor $102_1, 102_2, \ldots,$ or $102_M$ connected and dedicated thereto, from other sensors (e.g. the vibration sensor 104), and from the other channels' sensors, by means of one or more cross channel communication links as in 109. As such, in the event of sensor failure (e.g. due to disconnection of a signal line that may be caused by wire breaking), any given channel 108A, 108B, ..., 108N can continue to perform its control functions using input from the one or more other channels 108A, 108B, ..., 108N.

The control unit 106 may further comprise a detection unit 110 to which the channels 108A, 108B, ..., 108N are connected. As will be discussed further below, the detection unit 110 determines which ones of the speed sensors as in $102_1, 102_2, \ldots, 102_M$ are connected to each one of the channels as in 108A, 108B, ..., 108N at any given time. In this manner, it can be ensured that the correct speed sensors $102_1, 102_2, \ldots, 102_M$ are installed to the channels 108A, 108B, ..., 108N. The control unit 106 is further connected to the engine 10 via a link 112, which may be wired or wireless. Using the link 112, the control unit 106 may then output over a suitable network (not shown) control signals to the engine 10 for controlling the operation thereof.

Figure 3:
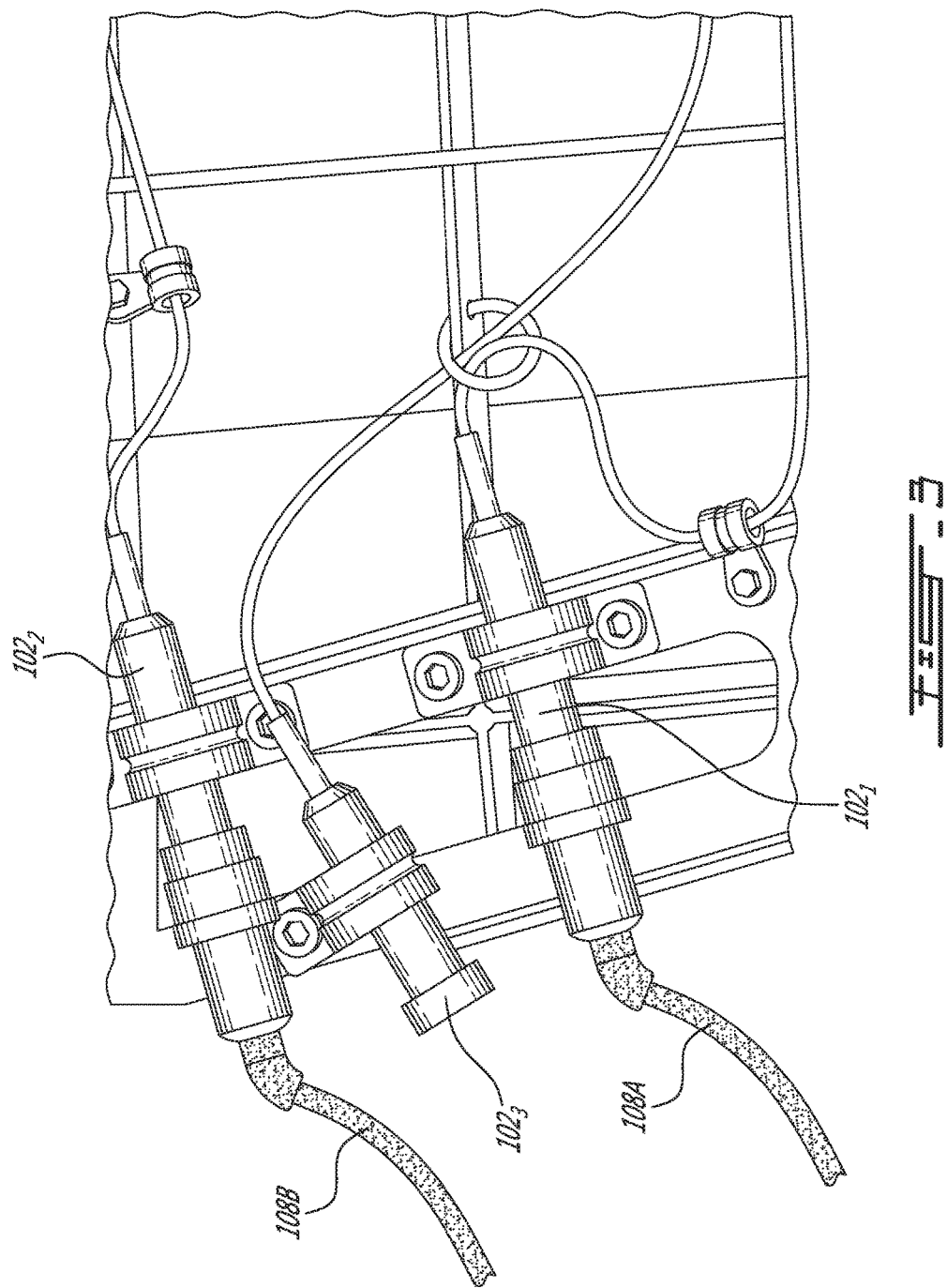
FIG. 3 is a perspective view showing sensors located in the engine of FIG. 1, in accordance with an illustrative embodiment.

Referring now to FIG. 3 in addition to FIG. 2, the control unit 106 illustratively comprises at least two of the channels as in 108A, 108B, ..., 108N and at least two of the speed sensors as in $102_1, 102_2, 102_3, \ldots, 102_M$ may therefore be provided. In one embodiment, one or more of the speed sensors $102_1, 102_2, 102_3, \ldots, 102_M$ are provided as redundant sensors for safety while the remaining ones of the speed sensors $102_1, 102_2, 102_3, \ldots, 102_M$ are used as primary sensors. In this configuration, each primary one of the speed sensors $102_1, 102_2, 102_3, \ldots, 102_M$, is connected to a corresponding channel 108A, 108B, ..., 108N. This is illustrated in FIG. 3 where the engine 10 comprises two control channels, namely channel A (reference 108A) and channel B (reference 108B) and two (2) of the three (3) speed sensors $102_1, 102_2,$ and $102_3$ provided in the system 100 are connected to the channels 108A, 108B at any given time for carrying sensor signals to the control unit 106. In particular, primary speed sensor $102_1$ may be connected to channel 108A while primary speed sensor $102_2$ is connected to channel 108B. Speed sensor $102_3$ is not connected to any of the channels 108A and 108B such that speed sensor $102_3$ is provided as a redundant or spare sensor should one of the primary speed sensors $102_1, 102_2$ fail.

Thus, in the embodiment shown in FIG. 3, the redundant sensor $102_3$ is normally not connected to the control unit (reference 106 in FIG. 2) but can be activated (e.g. manually) by a service technician or other personnel if a failure of one of the primary speed sensors $102_1$, $102_2$ occurs. For this purpose, in the event of such a failure, the failing primary speed sensor, i.e. speed sensor $102_1$ or $102_2$, may be disconnected from its corresponding channel 108A or 108B and the redundant speed sensor $102_3$ connected in its place. Although not illustrated, it should be understood that more than one redundant speed sensor as in $102_3$ may be provided at any given time. In this manner, failure of more than one primary speed sensor as in $102_1$, $102_2$ may be overcome. It should also be understood that, in some embodiments, no redundant speed sensors are provided.

Figure 4:
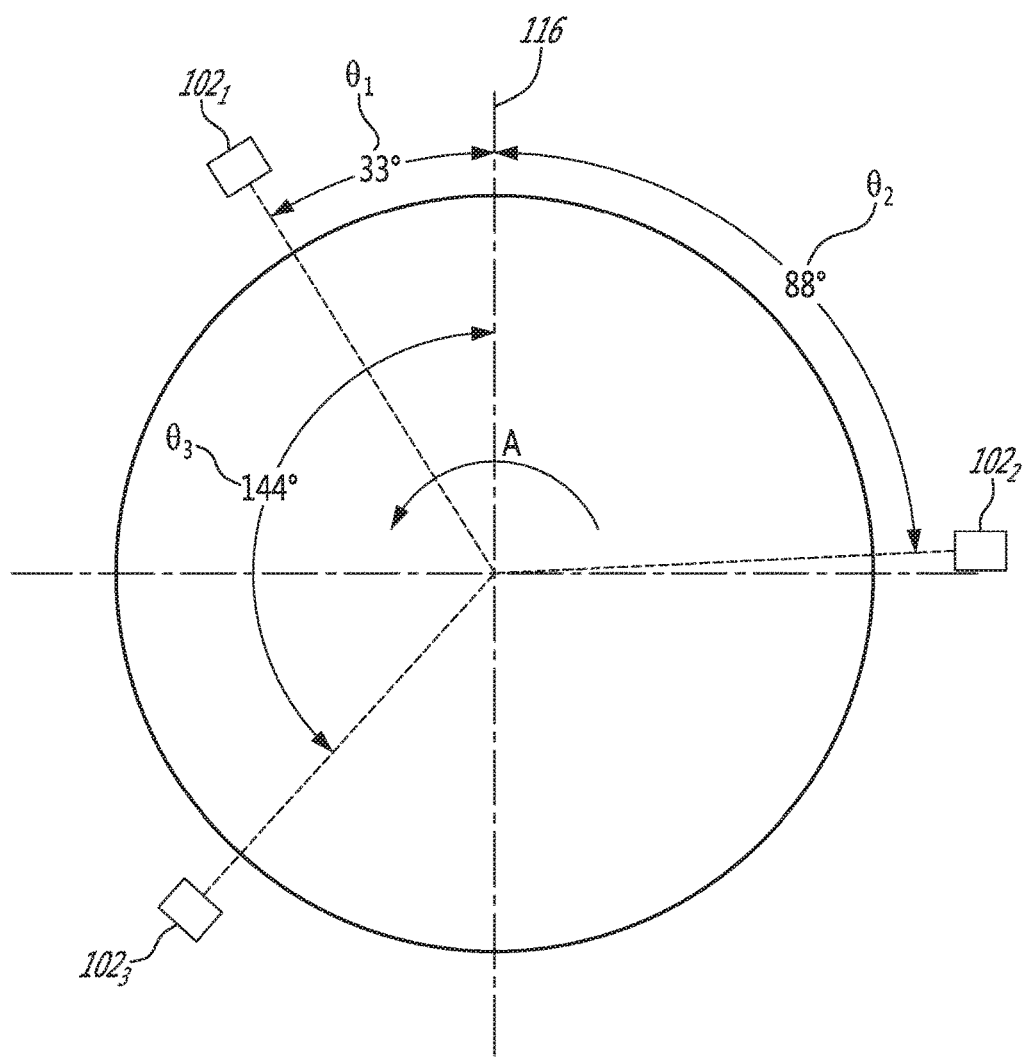
FIG. 4 is a schematic diagram illustrating circumferential sensor position, in accordance with an illustrative embodiment.

Referring now to FIG. 4 in addition to FIG. 2, the speed sensors $102_1$, $102_2$, $102_3$, . . . , $102_M$ are illustratively positioned circumferentially about a longitudinal axis (reference 114 on FIG. 1) of a shaft of the engine, which rotates along the direction of arrow A. The rotating engine shaft may be the low pressure shaft (reference 28 in FIG. 1) or the high pressure shaft (reference 24 in FIG. 1) and it should be understood that the speed sensors $102_1$, $102_2$, $102_3$, . . . , $102_M$ may be positioned around at least one of the shafts 24 and 28. As such, the speed sensors $102_1$, $102_2$, $102_3$, . . . , $102_M$ may be N1 sensors (for monitoring a speed of the low pressure shaft 28) and/or N2 sensors (for monitoring a speed of the high pressure shaft 24). In particular, N1 sensors may be installed adjacent to a phonic wheel (not shown) mounted at the rear of the low pressure shaft 28. Each N1 sensor may then generate an output signal proportional to the rotational speed of the low pressure turbine (i.e. the rotational speed of the low pressure shaft 28) N1. When N2 sensors are used, the latter may be installed near the high pressure shaft 24 and generate an output signal proportional to the rotational speed of the high pressure turbine (i.e. the rotational speed of the high pressure shaft 24).

The speed sensors $102_1$, $102_2$, $102_3$, . . . , $102_M$ illustratively have different angular positions, which may be measured relative to a fixed reference point of the engine 10. In one embodiment (illustrated in FIG. 4), the fixed reference point is the engine's top dead center (TDC) 116 but it should be understood that any other fixed point in the engine 10 may be used as a reference point. In the example shown in FIG. 4, the speed sensor $102_1$ is positioned at an angle $\theta_1$ of 33 degrees relative to the TDC 116, the speed sensor $102_2$ is positioned at an angle $\theta_2$ of 88 degrees relative to the TDC 116, and the speed sensor $102_3$ is positioned at an angle $\theta_3$ of 144 degrees relative to the TDC 116. It should be understood that other configurations may apply.

Figure 5:
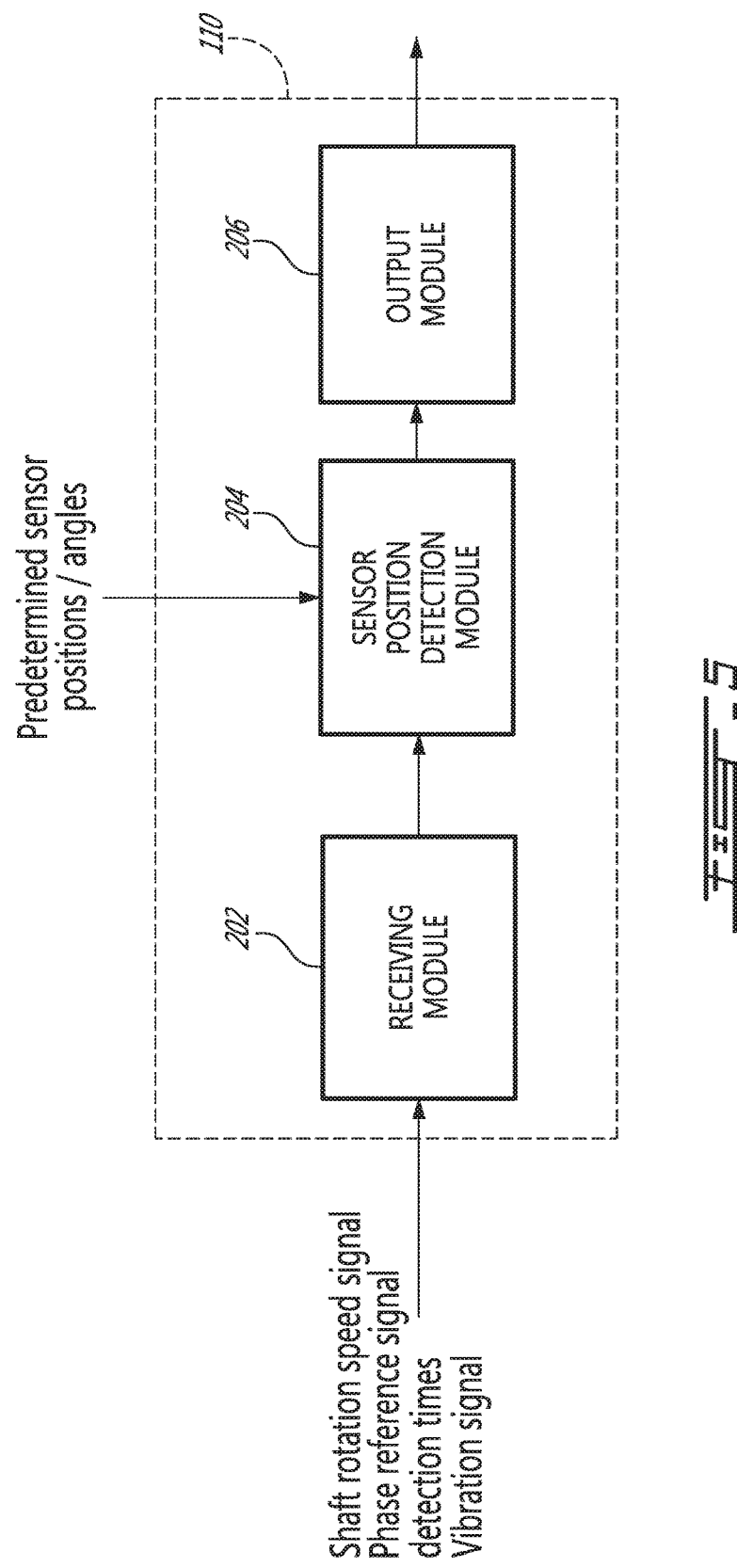
FIG. 5 is a schematic diagram of the detection unit of FIG. 2.

Referring to FIG. 5, the detection unit 110 illustratively comprises a receiving module 202, a sensor position detection module 204, and an output module 206.

The receiving module 202 illustratively receives from the speed sensors $102_1$, $102_2$, $102_3$, . . . , $102_M$ a shaft rotation speed signal indicative of a measurement of the rotation speed of the engine's rotating shaft (e.g. the low pressure shaft 28 or the high pressure shaft 24) taken at the time the sensor position detection calculation is performed by the detection unit 110.

The receiving module 202 may further receive data indicative of respective times at which a phase reference signal is received at the control channels (references 108A, 108B, . . . , or 108N in FIG. 2). When the speed sensors $102_1$, $102_2$, $102_3$, . . . , $102_M$ are installed around the low pressure shaft (reference 28 in FIG. 1), the phase reference signal may correspond to the detection (at a corresponding one of the channels 108A, 108B, . . . , or 108N) of the passage of a singularity of an N1 phonic wheel (not shown) integral with the low pressure shaft 28. A circumference of the phonic wheel is illustratively provided with a plurality of equally spaced teeth. A reader, such as a suitable inductive sensor having a varying reluctance or a Hall effect, may be arranged in a fixed position close to the phonic wheel. The reader is then adapted to read the passage of each tooth of the phonic wheel, and more particularly that of a singularity, such as an offset tooth or one or more missing teeth, provided in a predetermined angular position on the phonic wheel. The interval of time (or tooth time) which elapses between the passage of one tooth and the passage of the next tooth is continuously determined by the reader in order to determine the passage of the singularity. For instance, the passage of the singularity may be determined when a tooth time is bigger than the previous tooth time and the following tooth time. The reader may then output a phase reference signal that is then sent to the control unit 106 where it is received at the channels 108A, 108B, . . . , 108N. It should be understood that the phase reference channel may correspond to detection of any suitable event other than the passage of the N1 phonic wheel offset tooth.

Still referring to FIG. 5, the receiving module 202 may also receive a vibration signal comprising vibration measurements received from the vibration sensor (reference 104 in FIG. 2). The vibration sensor 104 is illustratively attached to the engine's casing and may be used to detect vibrations (e.g. vibrations associated with the low pressure shaft 28) of the engine (reference 10 in FIG. 2). For this purpose, the vibration sensor 104 may be any suitable vibration sensor, such as a piezoelectric accelerometer. The vibration sensor 104 then outputs to the control unit (reference 106 in FIG. 2) vibrations signals, which contain information corresponding to the vibrations detected.

The receiving module 202 illustratively transmits the received data to the sensor position detection module 204, which processes the received data to determine therefrom which ones of the speed sensors $102_1$, $102_2$, . . . , $102_M$ are connected to each one of the channels 108A, 108B, . . . , 108N at any given time. In some embodiments, the outcome of the processing performed by the sensor position detection module 204 (i.e. the detection information indicative of the sensor position and, optionally, of the computed phase and/or delta angle) may then be output to the output module 206 for transmission to and/or rendering on any suitable device, such as a maintenance computer, or the like (not shown), to be used for various purposes and applications. In other embodiments, the sensor position detection information output by the sensor position detection module 204 may be stored in memory for subsequent use. For instance, knowledge of which speed sensor as in $102_1$, $102_2$, . . . , or $102_M$ is connected to which channel as in 108A, 108B, . . . , or 108N may allow maintenance personnel to determine the speed sensor(s) to be replaced in case of sensor failure or fault. The sensor position detection information may alternatively be used for fan balancing (e.g. through an automated rotor balancing algorithm) or vibration monitoring. Other applications will be readily understood by a person skilled in the art.

Figure 6:
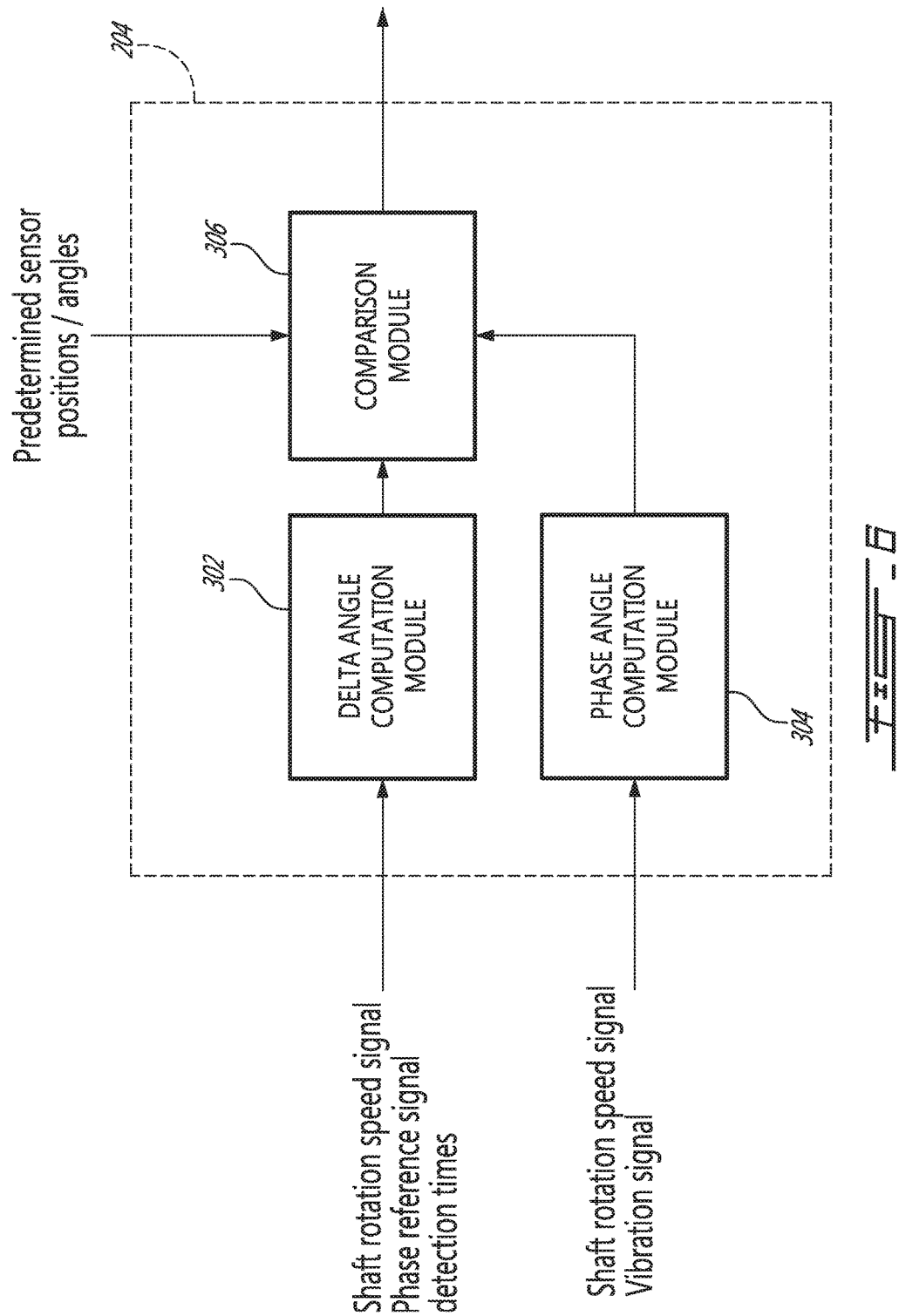
FIG. 6 is a schematic diagram of the sensor position detection module of FIG. 5.

Referring now to FIG. 6, the sensor position detection module 204 illustratively comprises a delta angle computation module 302, a phase angle computation module 304, and a comparison module 306. As will be discussed further below, it should be understood that at least one of the delta angle computation module 302 and the phase angle computation module 304 may be used to compute at least one operating parameter associated with the engine (i.e. a delta angle when the delta angle computation module 302 is used and/or a phase angle when the phase angle computation module 304 is used) and determine therefrom the sensor position detection information.

The delta angle computation module 302 illustratively receives from the receiving module 202 the phase reference signal detection times for all control channels 108A, 108B, ..., 108N. The delta angle computation module 302 may then compute the difference (or delta time) between the time at which the phase reference signal is received at a first one of the channels, e.g. channel 108A, and the time at which the phase reference signal is received at a second one of the channels, e.g. channel 108B. The delta angle computation module 302 may then extract the rotation speed measurement from the shaft rotation speed signal(s) received from the receiving module 202 and multiply the rotation speed measurement with the delta time to obtain the delta angle for the pair of channels 108A, 108B. It should be understood that when more than two (2) channels 108A, 108B are provided, the delta angle computation module 302 computes a delta time for pairs of the channels 108A, 108B, ..., 108N to obtain a corresponding delta angle value. It should also be understood that computations need not be performed for each channel pair so long as sufficient information is obtained to be able to determine the sensor position information therefrom. For instance, if three (3) channels 108A, 108B, and 108C are provided, the delta angle value need only be computed between channels 108A and 108B and channels 108C and 108A as this would provide the necessary information to determine the sensor positions.

The delta angle computation module 302 then sends the computed delta angle value(s) to the comparison module 306, which retrieves from the memory stored data indicative of a relationship between predetermined (or predicted) sensor positions and delta angle values. The predetermined sensor positions and delta angle values stored in the memory may be calculated using knowledge of the sensors' position (as illustrated in FIG. 4) relative to the engine's fixed reference point (e.g. the TDC 116). The stored data may be provided in a look-up table (or any other suitable) format, as shown in FIG. 7, where each predetermined delta angle value (or values when more than two of the control channels 108A, 108B, ..., 108N are provided) is associated with a predetermined sensor position combination or arrangement that identifies the one of the speed sensors (reference $102_1$, $102_2$, ..., $102_M$ in FIG. 2) connected to each one of the control channels (reference 108A, 108B, ..., 108N in FIG. 2). The comparison module 306 can then compare the computed (e.g. current) delta angle value(s) to each one of the predetermined delta angle values to identify the corresponding predetermined sensor position combination.

For instance, the comparison module 306 may retrieve the look-up table 400 of FIG. 7 and search the "Delta angle" column 402 to identify the predetermined delta angle value matching a given one of the computed delta angle value(s). It should be understood that in embodiments (discussed further below) where a phase angle is computed by the phase angle computation module 304, the data retrieved from memory would comprise predetermined phase angle values presented in a "Phase angle" column (not shown). In order to identify the matching predetermined delta angle value, the comparison module 306 may compute a difference between the given computed delta angle value and each predetermined delta angle value in column 402 and compare the difference to a predetermined hardware tolerance (e.g. four (4) degrees). The comparison module 306 concludes to a match between the given computed delta angle value and the present predetermined delta angle value if the difference is within the threshold (e.g. the computed delta angle value is not greater or lower than the present predetermined delta angle value by more the threshold value). Once a match is found, the comparison module 306 identifies the predetermined sensor position combination corresponding to the predetermined delta angle value. The comparison module 306 can then determine from the identified sensor position combination which ones of the speed sensors $102_1$, $102_2$, ..., $102_M$ are connected to each one of the channels 108A, 108B, ..., 108N.

For instance, in the example of FIG. 7, if the delta angle value output by the delta angle computation module 302 is 109.0 degrees and the tolerance four (4) degrees, the comparison module 306 determines from the look-up table 400 that the predetermined delta angle value is 111.0 degrees. The comparison module 306 then further determines from the look-up table 400 that case 1 applies, where sensor #1 (i.e. speed sensor $102_1$) is connected to channel A (i.e. channel 108A), as indicated in the "Channel A" column 404, while sensor #3 (i.e. speed sensor $102_3$) is connected to channel B (i.e. channel 108B), as indicated in the "Channel B" column 406. This further indicates that sensor $102_2$ is a redundant sensor.

Referring back to FIG. 6, the phase angle computation module 304 may be used when a vibration signal from the vibration sensor (reference 104 in FIG. 2) is available. If this is the case, the phase angle computation module 304 receives the shaft rotation speed signal(s) and the vibration signal from the receiving module (reference 202 in FIG. 5) and determines therefrom a phase angle relative to a position of the vibration sensor 104. In particular, the vibration signal may be correlated with the shaft rotation speed signal(s) in order to determine the phase angle.

The vibration signal received from the vibration sensor 104 (e.g. once per revolution of the low pressure shaft or the high pressure shaft, respectively references 28 and 24 in FIG. 1) illustratively has a sinusoidal wave profile of a given amplitude. The sinusoidal wave may be representative of oscillations detected over time as a result of motion of the rotating engine component(s) (e.g. the low pressure shaft 28 or the high pressure shaft 24) being monitored.

The shaft rotation speed signals received from the speed sensors (reference $102_1$, $102_2$, ..., $102_M$ in FIG. 2) may be obtained upon each speed sensor $102_1$, $102_2$, ..., $102_M$ detecting the passage of a singularity of the engine (e.g. an offset tooth, as discussed above). In one embodiment, the speed sensors $102_1$, $102_2$, ..., $102_M$ monitor the speed of the same rotating engine component, e.g. the low pressure shaft 28 or the high pressure shaft 24, such that the speed signals received at the the phase angle computation module 304 have the same frequency determined upon passage of the singularity. The frequency of the signals is also illustratively the same as the frequency of the vibrations signal received from the vibration sensor 104. Thus, at any given time, the passage of the singularity as detected by a given speed sensor, e.g. speed sensor $102_1$, corresponds to a given position within the cycle of oscillation, i.e. to a first amplitude data point, of the vibration signal. The passage of the singularity as detected by another speed sensor, e.g. speed sensor $102_2$, accordingly corresponds to a different position within the cycle of oscillation, i.e. to a second amplitude data point, of the vibration signal.

Because the speed sensors $102_1$, $102_2$, ..., $102_M$ are all installed at different positions in the engine 10, and therefore mounted at different positions relative to the vibration sensor 104, the signals detected by the speed sensors $102_1$, $102_2$, ..., $102_M$ are out of phase with one another by a given phase angle or difference. The value of the phase angle can then be computed by calculating the difference between the positions to which the signals detected by the sensors correspond. For instance, the value of the phase angle between speed sensors $102_1$ and $102_2$ can be obtained by computing the difference between the first and the second amplitude data points. In one embodiment, phase angle values need not be computed between each pair of speed sensors $102_1, 102_2, \ldots, 102_M$ so long as sufficient information is obtained to be able to determine the sensor position information therefrom. In one embodiment, the phase angle values need only be computed between M1 sensor pairs. For instance, if three (3) speed sensors $102_1$, $102_2$, $102_3$ are provided, a phase angle value need only be computed between speed sensors $102_1$ and $102_2$.

The phase angle computation module 304 may then send the computed (e.g. current) phase angle value(s) to the comparison module 306, which retrieves from the memory the stored data indicative of a relationship between the predetermined sensor positions and phase angle values. In a manner similar to that discussed above with reference to comparison on the basis of data received from the delta angle computation module 302, the comparison module 306 then compares the computed phase angle value(s) to each one of the predetermined phase angle values to identify the corresponding predetermined sensor position combination.

Referring now to FIG. 8, a method 500 for speed sensor position detection will now be described. The method 500 comprises determining at step 502 whether a vibration signal from a vibration sensor (reference 104 in FIG. 2) is available. If this is not the case, the method 500 may then flow to the step 504 of computing delta angle(s) seen between pairs of at least two control channels provided in the engine (reference 10 in FIG. 1). If it is determined at step 502 that a vibration signal is available, the method 500 may flow to the step 506 of computing phase angle(s). Although not illustrated, it should be understood that, after performing step 506, the method 500 may flow to the step 504 of computing delta angle(s) in addition to computation of the phase angle(s), e.g. for improving accuracy of the subsequent sensor position detection. After computing the phase angle(s) and/or the delta angle(s), the next step 508 may then be to determine, using the computed angle(s), the speed sensor connected to each one of the channels. Speed sensor position detection information, which is indicative of which speed sensor is connected to which control channel, may then be output at step 510. As discussed above, the speed sensor position detection information may be output to any suitable device (e.g. a maintenance computer) or to memory for storage therein.

Referring to FIG. 9, the step 504 of computing the delta angle(s) comprises obtaining at step 602 a measurement of the time at which a phase reference signal (e.g. detection of the N1 phonic wheel offset tooth, as discussed above) is received at a first channel. The next step 604 may be to obtain a measurement of the time when the phase reference signal is received at a second channel. The next step 606 may be to compute a difference between the times determined at steps 602 and 604, thereby obtaining the delta time. The shaft rotation speed measurement may then be obtained at step 608 and multiplied by the delta time computed at step 606 to obtain the delta angle between the first and the second channels at step 610. The next step 612 may then be to determine whether more than two channels are provided. If this is not the case, the method flows back to step 602 for computing the delta angle seen between other pairs of the channels. Otherwise, the method 500 flows to step 508.

Referring to FIG. 10, the step 508 of computing phase angle(s) comprises receiving at step 702 a vibration signal from a vibration sensor mounted to the engine. Shaft rotation speed signal(s) may then be received at step 704 and the vibration signal correlated therewith at step 706 in order to obtain the phase angle(s), in the manner discussed above with reference to FIG. 6.

Referring to FIG. 11, the step 508 of determining the speed sensor connected to each one of the channels may comprise obtaining at step 802 predetermined sensor positions and delta/phase angle values. This predetermined data may be provided in a look-up table format retrieved from memory, as discussed above with reference to FIG. 7. The next step 804 may then be to compare the delta/phase angle(s) computed at steps 504 and 506 to the predetermined sensor positions and delta/phase angles obtained at step 702 in order to identify at step 806 the speed sensor connected to each channel. This may be done in the manner discussed above with reference to FIG. 6 and FIG. 7. Once this is done, the speed sensor detection information may be output at step 510.

The above description is meant to be exemplary only, and one skilled in the art will recognize that changes may be made to the embodiments described without departing from the scope of the invention disclosed. Modifications which fall within the scope of the present invention will be apparent to those skilled in the art, in light of a review of this disclosure, and such modifications are intended to fall within the appended claims.

The invention claimed is:

1. A system for detection of speed sensor position in an engine, the engine comprising a plurality of speed sensors provided in different circumferential positions about at least one shaft of the engine, each one of the plurality of speed sensors configured for measuring a rotational speed of the at least one shaft, and a multi-channel controller having a plurality of control channels, each one of the plurality of control channels operatively connected to a different one of the plurality of speed sensors for providing sensor data to the multi-channel controller, the system comprising:
   a memory having stored therein:
      a plurality of predetermined sensor position arrangements, each identifying, for each one of the plurality of control channels, a selected one of the plurality of speed sensors connected to the control channel, and
      a plurality of predetermined values of at least one parameter associated with the engine, each of the plurality of predetermined values of the at least one parameter having associated therewith a corresponding one of the plurality of predetermined sensor position arrangements; and
   a processing unit adapted to:
      receive input data comprising the sensor data received from the plurality of speed sensors, the input data comprising a first shaft rotational speed signal indicative of rotational speed of the at least one shaft as measured by a first one of the plurality of speed sensors, a second shaft rotational speed signal indicative of rotational speed of the at least one shaft as measured by a second one of the plurality of speed sensors, and a vibration signal indicative of a vibration of the at least one shaft;
      compute on the basis of the input data a current value of the at least one parameter by:
         determining a first data point of the vibration signal corresponding to a first instance at which the first shaft rotational speed signal is measured by the first one of the plurality of speed sensors, determining a second data point of the vibration signal corresponding to a second instance at which the second shaft rotational speed signal is measured by the second one of the plurality of speed sensors, and computing the difference between the first data point and the second data point;

retrieve from the memory the plurality of predetermined sensor position arrangements and the plurality of predetermined values of the at least one parameter, determine a selected one of the plurality of predetermined values of the at least one parameter that matches the current value of the at least one parameter, and identify the corresponding one of the plurality of predetermined sensor position arrangements associated with the selected one of the plurality of predetermined values of the at least one parameter and determine therefrom, for each one of the plurality of control channels, the selected one of the plurality of speed sensors currently connected to the control channel.

2. The system of claim 1, wherein a number of the plurality of speed sensors is greater than a number of the plurality of control channels, the plurality of speed sensors comprising at least two primary speed sensors and at least one redundant speed sensor, and further wherein each one of the plurality of control channels has operatively connected thereto a different one of the at least two primary speed sensors.

3. The system of claim 1, wherein each one of the plurality of speed sensors is installed at a given angular position relative to a fixed reference point of the engine, and wherein the memory has stored therein the plurality of predetermined sensor position arrangements and the plurality of predetermined values of the at least one parameter computed on the basis of the given angular position of each one of the plurality of speed sensors relative to the fixed reference point.

4. The system of claim 3, wherein the memory has stored therein the plurality of predetermined values of the at least one parameter comprising at least one of a delta angle between at least one pair of the plurality of control channels and a phase angle seen between at least one pair of the plurality of speed sensors.

5. The system of claim 4, wherein the processing unit is adapted to receive the input data comprising a measurement of a current rotational speed of the at least one shaft as measured by each one of the plurality of speed sensors, a first time at which a phase reference signal is received at a first one of the plurality of control channels, and a second time at which the phase reference signal is received at a second one of the plurality of control channels, and further wherein the processing unit is adapted to compute the current value of the at least one parameter of the engine by computing a difference between the first time and the second time and multiplying the rotational speed measurement with the difference, thereby obtaining the current value of the delta angle between the first one and the second one of the plurality of control channels.

6. The system of claim 5, wherein the phase reference signal is received at a respective one of the first one and the second one of the plurality of control channels upon detection by a reader installed on the engine of passage of a singularity of a phonic wheel mounted to the at least one shaft.

7. The system of claim 4, wherein computing the difference between the first data point and the second data point comprises obtaining the current value of the phase angle seen between the first one and the second one of the plurality of speed sensors.

8. The system of claim 1, wherein the plurality of speed sensors are provided in different circumferential positions about the at least one shaft comprising at least one of a low pressure shaft of engine and a high pressure shaft of the engine.

9. The system of claim 1, wherein the processing unit is adapted to determine the selected one of the plurality of predetermined values of the at least one parameter that matches the current value of the at least one parameter comprising computing a difference between the current value of the at least one parameter and each one of the plurality of predetermined values of the at least one parameter, comparing the difference to a predetermined threshold, and identifying the one of the plurality of predetermined values of the at least one parameter as the selected one of the plurality of predetermined values of the at least one parameter if the difference is within the threshold.

10. The system of claim 1, wherein the processing unit is adapted to output detection data indicative of the selected one of the plurality of speed sensors connected to each one of the plurality of control channels, the detection data comprising the current value of the at least one parameter.

11. A method for detection of speed sensor position in an engine, the engine comprising a plurality of speed sensors provided in different circumferential positions about at least one shaft of the engine, each one of the plurality of speed sensors configured for measuring a rotational speed of the at least one shaft, and a multi-channel controller having a plurality of control channels, each one of the plurality of control channels operatively connected to a different one of the plurality of speed sensors for providing sensor data to the multi-channel controller, the method comprising:

storing a plurality of predetermined sensor position arrangements, each identifying, for each one of the plurality of control channels, a selected one of the plurality of speed sensors connected to the control channel, and a plurality of predetermined values of at least one parameter associated with the engine, each of the plurality of predetermined values of the at least one parameter having associated therewith a corresponding one of the plurality of predetermined sensor position arrangements;

receiving input data comprising the sensor data received from the plurality of speed sensors, the input data comprising a first shaft rotational speed signal indicative of rotational speed of the at least one shaft as measured by a first one of the plurality of speed sensors, a second shaft rotational speed signal indicative of rotational speed of the at least one shaft as measured by a second one of the plurality of speed sensors, and a vibration signal indicative of a vibration of the at least one shaft;

computing on the basis of the input data a current value of at least one parameter by:

determining a first data point of the vibration signal corresponding to a first instance at which the first shaft rotational speed signal is measured by the first one of the plurality of speed sensors, determining a second data point of the vibration signal corresponding to a second instance at which the second shaft rotational speed signal is measured by the second one of the plurality of speed sensors, and computing the difference between the first data point and the second data point;

retrieving the plurality of predetermined sensor position arrangements and the plurality of predetermined values of the at least one parameter;

determining a selected one of the plurality of predetermined values of the at least one parameter that matches the current value of the at least one parameter; and identifying the corresponding one of the plurality of predetermined sensor position arrangements associated with the selected one of the plurality of predetermined values of the at least one parameter and determining therefrom, for each one of the plurality of control channels, the selected one of the plurality of speed sensors currently connected to the control channel.

12. The method of claim 11, wherein receiving the input data comprises receiving the sensor data from the plurality of speed sensors comprising at least two primary speed sensors and at least one redundant speed sensor, each one of the plurality of control channels having operatively connected thereto a different one of the at least two primary speed sensors.

13. The method of claim 11, wherein storing the plurality of predetermined sensor position arrangements and the plurality of predetermined values of the at least one parameter comprises storing the plurality of predetermined sensor position arrangements and the plurality of predetermined values of the at least one parameter computed on the basis of a given angular position of each one of the plurality of speed sensors relative to a fixed reference point of the engine.

14. The method of claim 13, wherein storing the plurality of predetermined values of the at least one parameter comprises storing at least one of a delta angle between at least one pair of the plurality of control channels and a phase angle seen between at least one pair of the plurality of speed sensors.

15. The method of claim 14, wherein the input data is received as comprising a measurement of a current rotational speed of the at least one shaft as measured by a first one of the plurality of speed sensors, a first time at which a phase reference signal is received at a first one of the plurality of control channels, and a second time at which the phase reference signal is received at a second one of the plurality of control channels, and wherein computing the current value of the at least one parameter of the engine comprises computing a difference between the first time and the second time and multiplying the rotational speed measurement with the difference, thereby obtaining the current value of the delta angle between the first one and the second one of the plurality of control channels.

16. The method of claim 15, wherein the phase reference signal is received at a respective one of the first one and the second one of the plurality of control channels upon detection of passage of a singularity of a phonic wheel mounted to the at least one shaft.

17. The method of claim 14, wherein computing the difference between the first data point and the second date point comprises obtaining the current value of the phase angle seen between the first one and the second one of the plurality of speed sensors.

18. The method of claim 11, wherein determining the selected one of the plurality of predetermined values of the at least one parameter that matches the current value of the at least one parameter comprises computing a difference between the current value of the at least one parameter and each one of the plurality of predetermined values of the at least one parameter, comparing the difference to a predetermined threshold, and identifying the one of the plurality of predetermined values of the at least one parameter as the selected one of the plurality of predetermined values of the at least one parameter if the difference is within the threshold.

19. The method of claim 11, further comprising outputting detection data indicative of the selected one of the plurality of speed sensors connected to each one of the plurality of control channels, the detection data comprising the current value of the at least one parameter.

20. A system for detection of speed sensor position in an engine, the engine comprising a plurality of speed sensors provided in different circumferential positions about at least one shaft of the engine, each one of the plurality of speed sensors configured for measuring a rotational speed of the at least one shaft, and a multi-channel controller having a plurality of control channels, each one of the plurality of control channels operatively connected to a different one of the plurality of speed sensors for providing sensor data to the multi-channel controller, the system comprising:

means for storing a plurality of predetermined sensor position arrangements, each identifying, for each one of the plurality of control channels, a selected one of the plurality of speed sensors connected to the control channel, and a plurality of predetermined values of at least one parameter associated with the engine, each of the plurality of predetermined values of the at least one parameter having associated therewith a corresponding one of the plurality of predetermined sensor position arrangements;

means for receiving input data comprising the sensor data received from the plurality of speed sensors, the input data comprising a first shaft rotational speed signal indicative of rotational speed of the at least one shaft as measured by a first one of the plurality of speed sensors, a second shaft rotational speed signal indicative of rotational speed of the at least one shaft as measured by a second one of the plurality of speed sensors, and a vibration signal indicative of a vibration of the at least one shaft;

means for computing on the basis of the input data a current value of at least one parameter by:
determining a first data point of the vibration signal corresponding to a first instance at which the first shaft rotational speed signal is measured by the first one of the plurality of speed sensors,
determining a second data point of the vibration signal corresponding to a second instance at which the second shaft rotational speed signal is measured by the second one of the plurality of speed sensors, and computing the difference between the first data point and the second data point;

means for retrieving the plurality of predetermined sensor position arrangements and the plurality of predetermined values of the at least one parameter;

means for determining a selected one of the plurality of predetermined values of the at least one parameter that matches the current value of the at least one parameter; and means for identifying the corresponding one of the plurality of predetermined sensor position arrangements associated with the selected one of the plurality of predetermined values of the at least one parameter and determining therefrom, for each one of the plurality of control channels, the selected one of the plurality of speed sensors currently connected to the control channel.

* * * * *